United States Patent
Ogura

(10) Patent No.: US 6,733,460 B2
(45) Date of Patent: May 11, 2004

(54) ARTERIOSCLEROSIS DIAGNOSING APPARATUS

(75) Inventor: Toshihiko Ogura, Komaki (JP)

(73) Assignee: Colin Medical Technology Corporation, Komaki (JP)

( * ) Notice: Subject to any disclaimer, the term of this patent is extended or adjusted under 35 U.S.C. 154(b) by 0 days.

(21) Appl. No.: 10/193,899

(22) Filed: Jul. 15, 2002

(65) Prior Publication Data

US 2003/0109788 A1 Jun. 12, 2003

(30) Foreign Application Priority Data

Dec. 12, 2001 (JP) ........................................ 2001-378839

(51) Int. Cl.[7] .............................................. A61B 5/02
(52) U.S. Cl. ........................ 600/490; 600/491; 600/500
(58) Field of Search ................................. 600/490, 481, 600/485, 491, 493, 494, 495, 496, 500, 501, 502

(56) References Cited

U.S. PATENT DOCUMENTS

| | | | |
|---|---|---|---|
| 5,865,756 A | 2/1999 | Peel, III | |
| 5,931,790 A | 8/1999 | Peel, III | |
| 6,379,309 B1 | 4/2002 | Ogura et al. | 600/490 |
| 6,517,493 B2 | 2/2003 | Ogura et al. | 600/490 |
| 6,524,257 B2 * | 2/2003 | Ogura | 600/490 |
| 6,565,515 B2 * | 5/2003 | Ogura | 600/494 |
| 6,612,993 B2 * | 9/2003 | Narimatsu | 600/500 |

FOREIGN PATENT DOCUMENTS

| | | |
|---|---|---|
| DE | 199 60 452 A1 | 8/2001 |
| EP | 0 990 418 A1 | 4/2000 |
| EP | 1 050 267 A1 | 11/2000 |
| EP | 1 203 558 A2 | 5/2002 |
| JP | A-57-134141 | 8/1982 |
| JP | A-62-34531 | 2/1987 |
| JP | A-10-179528 | 7/1998 |
| JP | B2-2938238 | 6/1999 |
| JP | B1-3027750 | 1/2000 |
| JP | B2 3140007 | 12/2000 |
| JP | A-2001-506166 | 5/2001 |
| JP | A-2001-161650 | 6/2001 |
| WO | WO 98/55020 | 12/1998 |

* cited by examiner

*Primary Examiner*—Max F. Hindenburg
*Assistant Examiner*—Navin Natnithithadha
(74) *Attorney, Agent, or Firm*—Oliff & Berridge, PLC

(57) ABSTRACT

An apparatus for diagnosing arteriosclerosis of a living subject, including an inflatable cuff which is adapted to be wound around a first portion of the subject to press the first portion with a pressing pressure, a pulse-wave detecting device which detects a pulse wave that is produced from an artery of the first portion of the subject pressed by the cuff with the pressing pressure and is transmitted to the cuff, and an arteriosclerosis judging device for judging, based on a change of the pulse wave caused by a change of the pressing pressure of the cuff, whether there is an arteriosclerotic lesion in a second portion of the subject that is located upstream of the first portion in a direction in which blood flows in the artery.

10 Claims, 6 Drawing Sheets

ARTERIOSCLEROSIS DIAGNOSING APPARATUS

BACKGROUND OF THE INVENTION

1. Field of the Invention

The present invention relates to an arteriosclerosis diagnosing apparatus for diagnosing arteriosclerosis or arteriosclerotic lesion, in particular, atherosclerosis.

2. Related Art Statement

There are known three sorts of arteriosclerosis; atherosclerosis is atheromatous sclerosis of endothelium of large or medium arteries, mediosclerosis is calcification of media of arteries, and arteriolosclerosis is sclerosis of small arteries.

Meanwhile, pulse-wave-propagation-velocity-related information that is related to a velocity at which a pulse wave propagates between two regions of a living subject, e.g., pulse-wave propagation velocity itself or pulse-wave propagation time, may be measured to diagnose whether the subject has atherosclerosis or not, or what degree of atherosclerosis the subject has. If a pulse-wave propagation velocity as a sort of pulse-wave-propagation-velocity-related information is measured from an atherosclerotic region of the subject, the measured velocity is higher than a normal velocity, if a degree of the atherosclerosis is low; and the measured velocity is lower than the normal velocity, if the degree of atherosclerosis is medium or high. Thus, the pulse-wave-propagation-velocity-related information can be used to diagnose whether the subject has atherosclerosis, or what degree of atherosclerosis the subject has.

The reason why a measured pulse-wave propagation velocity is higher than a normal velocity if a degree of atherosclerosis is low and the measured velocity is lower than the normal velocity if the degree of atherosclerosis is medium or high, is as follows: As atherosclerosis that is also called arteriostenosis advances, the inner diameters of arteries decrease. Since blood pressure lowers downstream of the arteriostenotic region, pulse-wave propagation velocity that changes with the blood pressure also lowers. Meanwhile, since mediosclerosis is calcification of media, the pulse-wave propagation velocity increases as the mediosclerosis advances. Generally, the mediosclerosis advances with the atherosclerosis. In the case where the degree of atherosclerosis is low, the influence of mediosclerosis is stronger than that of the atherosclerosis and accordingly the pulse-wave propagation velocity is higher than the normal velocity. However, in the case where the degree of atherosclerosis is medium or high, the influence of atherosclerosis is stronger than that of the mediosclerosis and accordingly the pulse-wave propagation velocity is lower than the normal velocity.

Pulse-wave propagation velocity has the above-described relationship with atherosclerosis and mediosclerosis. Since, however, the present invention relates to an apparatus for diagnosing atherosclerosis or arteriostenosis, the following description employs such a definition that arteriosclerosis means atherosclerosis, unless it otherwise specifies.

There is known an inferior-and-superior-limb blood-pressure-index measuring apparatus as a sort of arteriosclerosis diagnosing apparatus. This apparatus is disclosed in, e.g., Japanese Patent No. 3,140,007 or its corresponding U.S. Pat. No. 6,355,000. The inferior-and-superior-limb blood-pressure-index measuring apparatus includes two cuffs that are adapted to be worn on an inferior limb and a superior limb of a living subject, calculates, as an inferior-and-superior-limb blood-pressure-index, a ratio of one of a superior-limb blood pressure and an inferior-limb blood pressure to the other, and diagnoses arteriosclerosis based on the thus calculated inferior-and-superior-limb blood-pressure-index. If this apparatus is so modified as to be able to obtain pulse-wave-propagation-velocity-related information so as to assure the reliability of inferior-and-superior-limb blood-pressure-index, then the apparatus would be able to more accurately diagnose arteriosclerosis. If the two cuffs employed to measure the superior-limb blood pressure and the inferior-limb blood pressure are used to detect respective pulse waves from the superior limb and the inferior limb, the thus detected two pulse waves would be able to be used to determine a pulse-wave propagation time. Thus, the pulse-wave propagation time as another sort of pulse-wave-propagation-velocity-related information would be able to be obtained without needing to employing any additional sensors.

In many cases, arteriosclerosis occurs to inferior limbs only. However, in some cases, arteriosclerosis occurs to superior limbs as well. A pulse-wave propagation time measured from a superior limb and an inferior limb means a difference between a time of propagation of a pulse wave from the heart to the superior limb and a time of propagation of the pulse wave from the heart to the inferior limb. Therefore, in those cases, even if the inferior limb has arteriosclerosis and accordingly a time of propagation of pulse wave from the heart to the inferior limb increases, a pulse-wave propagation time measured from the superior limb and the inferior limb, or a pulse-wave propagation velocity determined based on the measured propagation time falls in a normal range, if the superior limb has arteriosclerosis and accordingly a time of propagation of pulse wave from the heart to the superior limb increases. Thus, in the above-indicated cases, the pulse-wave-propagation-velocity-related information obtained from the superior and inferior limbs cannot be used to diagnose arteriosclerosis with high accuracy.

Meanwhile, there are some cases where noise produced by a physical motion of a living subject is mixed with pulse waves and accordingly respective reference points of those pulse waves that are to be used to obtain pulse-wave propagation-velocity-related information cannot be accurately detected. In those cases, the pulse-wave-propagation-velocity-related information cannot be obtained with accuracy. In addition, if arrhythmia occurs to a living subject, respective reference points of two pulse waves to be used to obtain pulse-wave propagation-velocity-related information may not be accurately detected, and accordingly the pulse-wave-propagation-velocity-related information may not be obtained with accuracy. If pulse-wave-propagation-velocity-related information cannot be obtained with accuracy, then arteriosclerotic legion cannot be diagnosed with accuracy.

SUMMARY OF THE INVENTION

It is therefore an object of the present invention to provide an arteriosclerosis diagnosing apparatus for diagnosing arteriosclerosis or arteriosclerotic lesion with high accuracy.

The above object has been achieved by the present invention. According to a first aspect of the present invention, there is provided an apparatus for diagnosing arteriosclerosis of a living subject, comprising an inflatable cuff which is adapted to be wound around a first portion of the subject to press said first portion with a pressing pressure; a pulse-wave detecting device which detects a pulse wave that is produced from an artery of said first portion of the subject pressed by the cuff with the pressing pressure and is transmitted to the cuff; and an arteriosclerosis judging means for judging, based on a change of the pulse wave caused by a change of the pressing pressure of the cuff, whether there is an arteriosclerotic lesion in a second portion of the subject that is located upstream of said first portion in a direction in which blood flows in the artery.

If the subject has arteriosclerosis in the second portion located upstream of the first portion around which the cuff is wound, the sharpness of shape of the pulse wave detected from the first portion by the pulse-wave detecting device significantly decreases at a lower pressing pressure of the cuff than a pressing pressure at which the sharpness of shape of a pulse wave detected from a first portion located downstream of a second portion free of arteriosclerosis significantly decreases. Therefore, the arteriosclerosis judging means can judge, based on the change of the pulse wave caused by the change of the pressing pressure of the cuff, whether there is arteriosclerosis in the second portion located upstream of the first portion around which the cuff is wound.

If the above-described principle is applied to the left and right superior limbs, arteriosclerosis of an inferior limb can be accurately diagnosed based on pulse-wave-propagation-velocity-related information obtained from the inferior limb and one of the two superior limbs. According to a second aspect of the present invention, there is provided an apparatus for diagnosing arteriosclerosis of an inferior limb of a living subject, comprising a left-superior-limb cuff which is adapted to be wound around a left superior limb of the subject to press the left superior limb with a first pressing pressure; a right-superior-limb cuff which is adapted to be wound around a right superior limb of the subject to press the right superior limb with a second pressing pressure; an inferior-limb cuff which is adapted to be wound around the inferior limb of the subject; a left-superior-limb pulse-wave detecting device which detects, as a left-superior-limb pulse wave, a pulse wave which is produced from an artery of the left superior limb pressed by the left-superior-limb cuff with the first pressing pressure and is transmitted to the left-superior-limb cuff; a right-superior-limb pulse-wave detecting device which detects, as a right-superior-limb pulse wave, the pulse wave which is produced from an artery of the right superior limb pressed by the right-superior-limb cuff with the second pressing pressure and is transmitted to the right-superior-limb cuff; an inferior-limb pulse-wave detecting device which detects, as an inferior-limb pulse wave, the pulse wave which is produced from an artery of the inferior limb pressed by the inferior-limb cuff and is transmitted to the inferior-limb cuff; a change-value calculating means for calculating a first change value representing a change of the left-superior-limb pulse wave caused by a change of the first pressing pressure of the left-superior-limb cuff, and a second change value representing a change of the right-superior-limb pulse wave caused by a change of the second pressing pressure of the right-superior-limb cuff; an arteriosclerosis judging means for judging, based on a comparison of the first and second change values calculated by the change-value calculating means, which is lower, a degree of arteriosclerosis of a first portion of the subject located between the heart of the subject and the left superior limb or a degree of arteriosclerosis of a second portion of the subject located between the heart and the right superior limb; and a pulse-wave-propagation-velocity-related-information obtaining means for obtaining, based on (a) one of the left-superior-limb pulse wave and the right-superior-limb pulse wave that corresponds to one of the first and second portions that has the degree of arteriosclerosis judged as being lower than the degree of arteriosclerosis of the other of the first and second portions by the arteriosclerosis judging means, and (b) the inferior-limb pulse wave detected by the inferior-limb pulse-wave detecting device, pulse-wave-propagation-velocity-related information that is related to a velocity at which the pulse wave propagates in the subject.

According to this aspect, the change-value calculating means calculates the first and second change values. The first change value represents the change of the left-superior-limb pulse wave caused by the change of the first pressing pressure of the left-superior-limb cuff, and the second change value represents the change of the right-superior-limb pulse wave caused by the change of the second pressing pressure of the right-superior-limb cuff. Thus, the first change value reflects a degree of arteriosclerosis of the first portion of the subject located between the heart and the left superior limb, and the second change value reflects a degree of arteriosclerosis of the second portion of the subject located between the heart and the right superior limb. Therefore, the arteriosclerosis judging means can judge, by comparing the first and second change values with each other, which is lower, the degree of arteriosclerosis of the first portion located between the heart and the left superior limb or the degree of arteriosclerosis of the second portion located between the heart and the right superior limb. The pulse-wave-propagation-velocity-related-information obtaining means obtains, based on the superior-limb pulse wave corresponding to one of the first and second portions that has the degree of arteriosclerosis judged as being lower by the arteriosclerosis judging means, and the inferior-limb pulse wave, the pulse-wave-propagation-velocity-related information. Thus, the present apparatus can obtain the pulse-wave-propagation-velocity-related information that is less influenced by the arteriosclerosis of the superior limbs. Therefore, the pulse-wave-propagation-velocity-related information can be used to diagnose accurately arteriosclerosis of the inferior limb.

According to a third aspect of the present invention, there is provided an apparatus for diagnosing arteriosclerosis of a living subject, comprising a first-pulse-wave detecting device including a first detecting portion which is adapted to be worn on a first body portion of the subject to detect, as a first pulse wave, a pulse wave produced from the first body portion; a second-pulse-wave detecting device including a second detecting portion which is adapted to be worn on a second body portion of the subject to detect, as a second pulse wave, the pulse wave produced from the second body portion; a synchronism judging means for judging whether the first pulse wave detected by the first-pulse-wave detecting device and the second pulse wave detected by the second-pulse-wave detecting device are synchronous with each other; and a pulse-wave-propagation-velocity-related-information obtaining means for obtaining, based on the first and second pulse waves judged as being synchronous with each other by the synchronism judging means, pulse-wave-propagation-velocity-related information that is related to a velocity at which the pulse wave propagates in the subject.

When noise is produced by a physical motion of the living subject, it may be mixed, at different timings, with two pulse waves detected from different regions of the subject. In this case, respective detected pulses of the two pulse waves may not be synchronous with each other. However, if the synchronism judging means judges that first pulse wave detected by the first pulse-wave detecting device and the second pulse wave detected by the second pulse-wave detecting device are synchronous with each other, then it can be said that the first and second pulse waves are free of the noise produced by the physical motion of the subject. The pulse-wave-propagation-velocity-related-information obtaining means obtains the pulse-wave-propagation-velocity-related information based on the first and second pulse waves judged as being synchronous with each other by the synchronism judging means. Thus, the present apparatus can obtain accurate pulse-wave-propagation-velocity-related information. Therefore, arteriosclerosis can be accurately diagnosed based on the thus obtained, accurate pulse-wave-propagation-velocity-related information.

According to a fourth aspect of the present invention, there is provided an apparatus for diagnosing arteriosclerosis of a living subject, comprising a first-pulse-wave detecting device including a first detecting portion which is adapted to be worn on a first body portion of the subject to detect, as a first pulse wave, a pulse wave produced from the first body portion; a second-pulse-wave detecting device including a second detecting portion which is adapted to be worn on a second body portion of the subject to detect, as a second pulse wave, the pulse wave produced from the second body portion; a normal-pulse-period-range determining means for determining a normal pulse-period range based on one of the first pulse wave detected by the first-pulse-wave detecting device and the second pulse wave detected by the second-pulse-wave detecting device; an arrhythmia judging means for judging, when one of a pulse period of the first pulse wave and a pulse period of the second pulse wave falls in the normal pulse-period range determined by the normal-pulse-period-range determining means, that the first and second pulse waves are not arrhythmic; and a pulse-wave-propagation-velocity-related-information obtaining means for obtaining, based on the first and second pulse waves judged as being not arrhythmic by the arrhythmia judging means, pulse-wave-propagation-velocity-related information that is related to a velocity at which the pulse wave propagates in the subject.

According to this aspect, the pulse-wave-propagation-velocity-related-information obtaining means obtains the pulse-wave-propagation-velocity-related information based on the first and second pulse waves judged as being not arrhythmic by the arrhythmia judging means. Thus, the present apparatus can obtain accurate pulse-wave-propagation-velocity-related information. Therefore, arteriosclerosis can be accurately diagnosed based on the thus obtained, accurate pulse-wave-propagation-velocity-related information.

BRIEF DESCRIPTION OF THE DRAWINGS

The above and optional objects, features, and advantages of the present invention will be better understood by reading the following detailed description of the preferred embodiments of the invention when considered in conjunction with the drawings, in which.

DETAILED DESCRIPTION OF PREFERRED EMBODIMENTS

Figure 1:
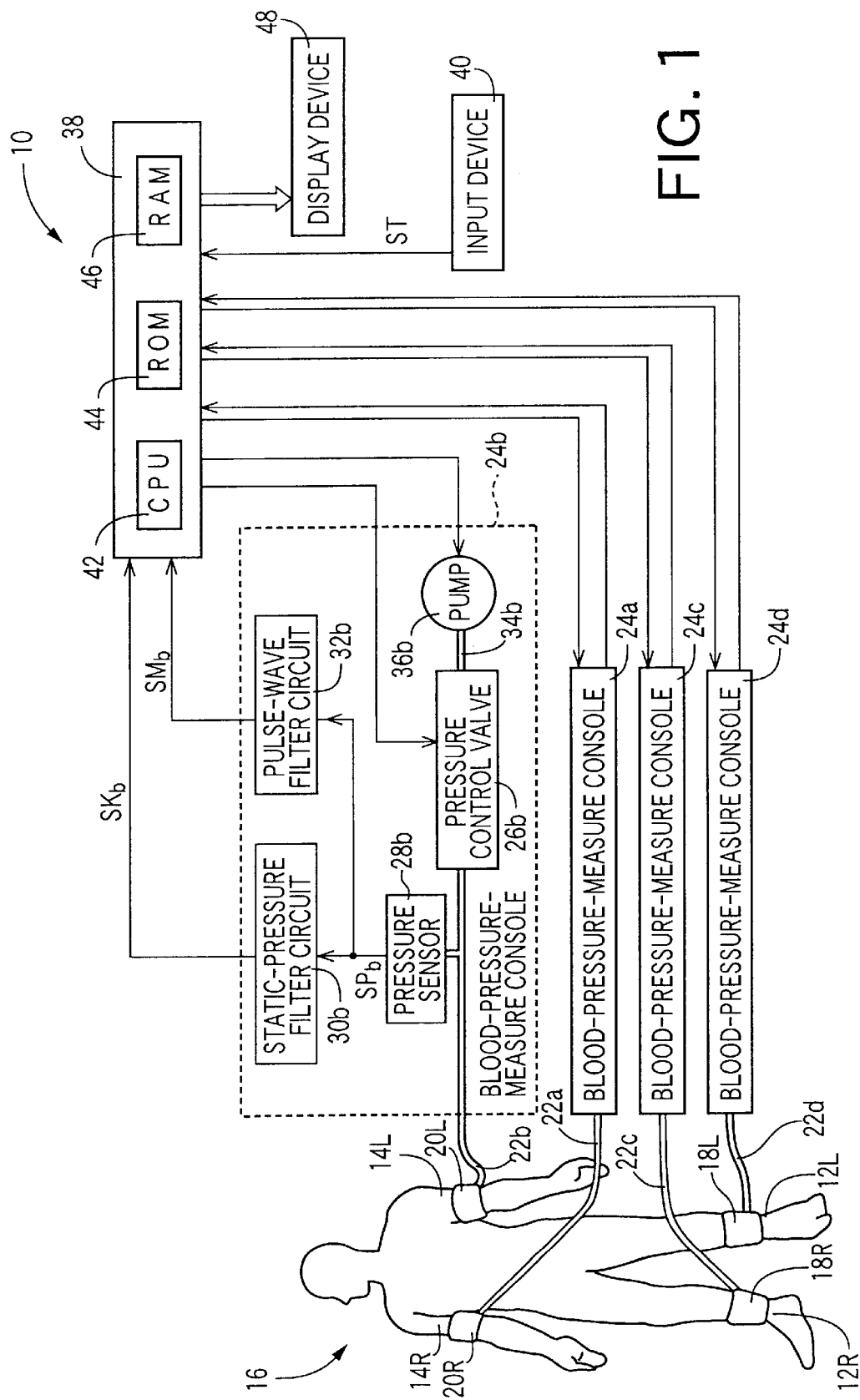
FIG. 1 is a diagrammatic view for explaining a construction of an arteriosclerosis diagnosing apparatus to which the present invention is applied.

Hereinafter, there will be described an embodiment of the present invention in detail by reference to the drawings. FIG. 1 shows a diagrammatic view for explaining a construction of an arteriosclerosis diagnosing apparatus 10 to which the present invention is applied. The present arteriosclerosis diagnosing apparatus 10 also functions as an ankle-arm blood pressure index measuring apparatus.

In FIG. 1, the arteriosclerosis diagnosing apparatus 10 includes a left ankle cuff 18L and a right ankle cuff 18R which are wound around a left ankle 12L and a right ankle 12R, respectively, of a patient 16, and a left upper-arm cuff 20L and a right upper-arm cuff 20R which are wound around a left upper arm 14L and a right upper arm 14R, respectively, of the patient 16. Each of the cuffs 18, 20 functions as a pressing band which presses a portion of the patient around which the each cuff is wound, and includes a belt-like outer bag which is formed of a non-stretchable material such as cloth or polyester; and a rubber bag accommodated in the outer bag.

The left and right upper-arm cuffs 20L, 20R are connected via respective pipings 22b, 22a to respective blood-pressure-measure consoles 24b, 24a; and the left and right ankle cuffs 18L, 18R are connected via respective pipings 22d, 22c to respective blood-pressure-measure consoles 24d, 24c.

Since the four blood-pressure-measure consoles 24a, 24b, 24c, 24d have an identical construction, the blood-pressure-measure console 24b to which the left upper-arm cuff 20L is connected will be described below as a representative of the four devices 24. The blood-pressure-measure console 24b includes a pressure control valve 26b, a pressure sensor 28b, a static-pressure filter circuit 30b, a pulse-wave filter circuit 32b, a piping 34b, and an air pump 36b, and the piping 22b is connected to the pressure control valve 26b and the pressure sensor 28b. The pressure control valve 26b is connected via the piping 34b to the air pump 36b.

The pressure control valve 26b controls or adjusts a pressure of a pressurized air supplied from the air pump 36b, so as to supply the pressure-adjusted air to the left upper-arm cuff 20L, and discharges the pressurized air from the left upper-arm cuff 20L, so as to control the air pressure in the cuff 20L.

The pressure sensor 28b detects the air pressure in the left upper-arm cuff 20L, and supplies a pressure signal, $SP_b$, representing the detected air pressure, to the static-pressure filter circuit 30b and the pulse-wave filter circuit 32b. The static-pressure filter circuit 30b includes a low-pass filter which extracts, from the pressure signal $SP_b$, a cuff-pressure signal, $SK_b$, representing a static component of the detected pressure, i.e., a pressing pressure of the cuff 20L (hereinafter, referred to as the left-upper-arm cuff pressure, $PC_b$). The filter circuit 30b supplies the cuff-pressure signal $SK_b$ to an electronic control device 38 via an A/D (analog-to-digital) converter, not shown.

The pulse-wave filter circuit 32b includes a band-pass filter which extracts, from the pressure signal $SP_b$, a left-upper-arm pulse-wave signal, $SM_b$, representing a left-upper-arm pulse wave $WB_L$ as an oscillatory component of the detected pressure that has prescribed frequencies. The filter circuit 32b supplies the pulse-wave signal $SM_b$ to the control device 38 via an A/D converter, not shown. Since the pulse-wave signal $SM_b$ represents the left-upper-arm pulse wave $WB_L$ produced from an artery of the left upper arm 14L pressed by the left upper-arm cuff 20L, the left upper-arm cuff 20L and the blood-pressure-measure console 24b cooperate with each other to function as a left-upper-arm-pulse-wave detecting device. The left-upper-arm pulse wave $WB_L$ is a first pulse wave, and accordingly the left upper-arm cuff 20L and the blood-pressure-measure console 24b also function as a first-pulse-wave detecting device.

Similarly, a right-upper-arm pulse wave $WB_R$ represented by a right-upper-arm pulse-wave signal $SM_a$ extracted by a pulse-wave filter circuit 32a is a first pulse wave, and accordingly the right upper-arm cuff 20R and the blood-pressure-measure console 24a cooperate with each other to function as a right-upper-arm-pulse-wave detecting device and also function as a first-pulse-wave detecting device.

Moreover, a left-ankle pulse wave $WA_L$ represented by a left-ankle pulse-wave signal $SM_d$ extracted by a pulse-wave filter circuit 32d is a second pulse wave, and accordingly the left ankle cuff 18L and the blood-pressure-measure console 24d cooperate with each other to function as a left-ankle-pulse-wave detecting device and also function as a second-pulse-wave detecting device. Similarly, a right-ankle pulse wave $WA_R$ represented by a right-ankle pulse-wave signal $SM_c$ extracted by a pulse-wave filter circuit 32c is a second pulse wave, and accordingly the right ankle cuff 18R and the blood-pressure-measure console 24c cooperate with each other to function as a right-ankle-pulse-wave detecting device and also function as a second-pulse-wave detecting device.

An input device 40 has a plurality of numeric keys, not shown, which are manually operable by a person to input a height, T, of the patient, and supplies a height signal, ST, representing the inputted patient's height T, to the control device 38.

The control device 38 is essentially provided by a microcomputer including a CPU (central processing unit) 42, a ROM (read only memory) 44, a RAM (random access memory) 46, and an I/O (input-and-output) port, not shown. The CPU 42 processes signals according to the control programs pre-stored in the ROM 44, while utilizing the temporary-storage function of the RAM 46, and the CPU 42 outputs, from the I/O port, drive signals to the respective air pumps 36 and respective pressure control valves 26 of the four blood-pressure-measure consoles 24, so as to control the respective operations of those elements 36, 26 and thereby control the respective pressures in the cuffs 18, 20. In addition, the CPU 42 obtains and determines, based on the signals supplied to the control device 38, a piece of pulse-wave-propagation-related information, and an inferior-and-superior-limb blood-pressure index (e.g., an ankle-arm blood-pressure index; hereinafter, abbreviated to ABI) of the patient. In addition, the CPU 42 controls a display device 48 to display the thus obtained information and thus determined index ABI.

Figure 2:
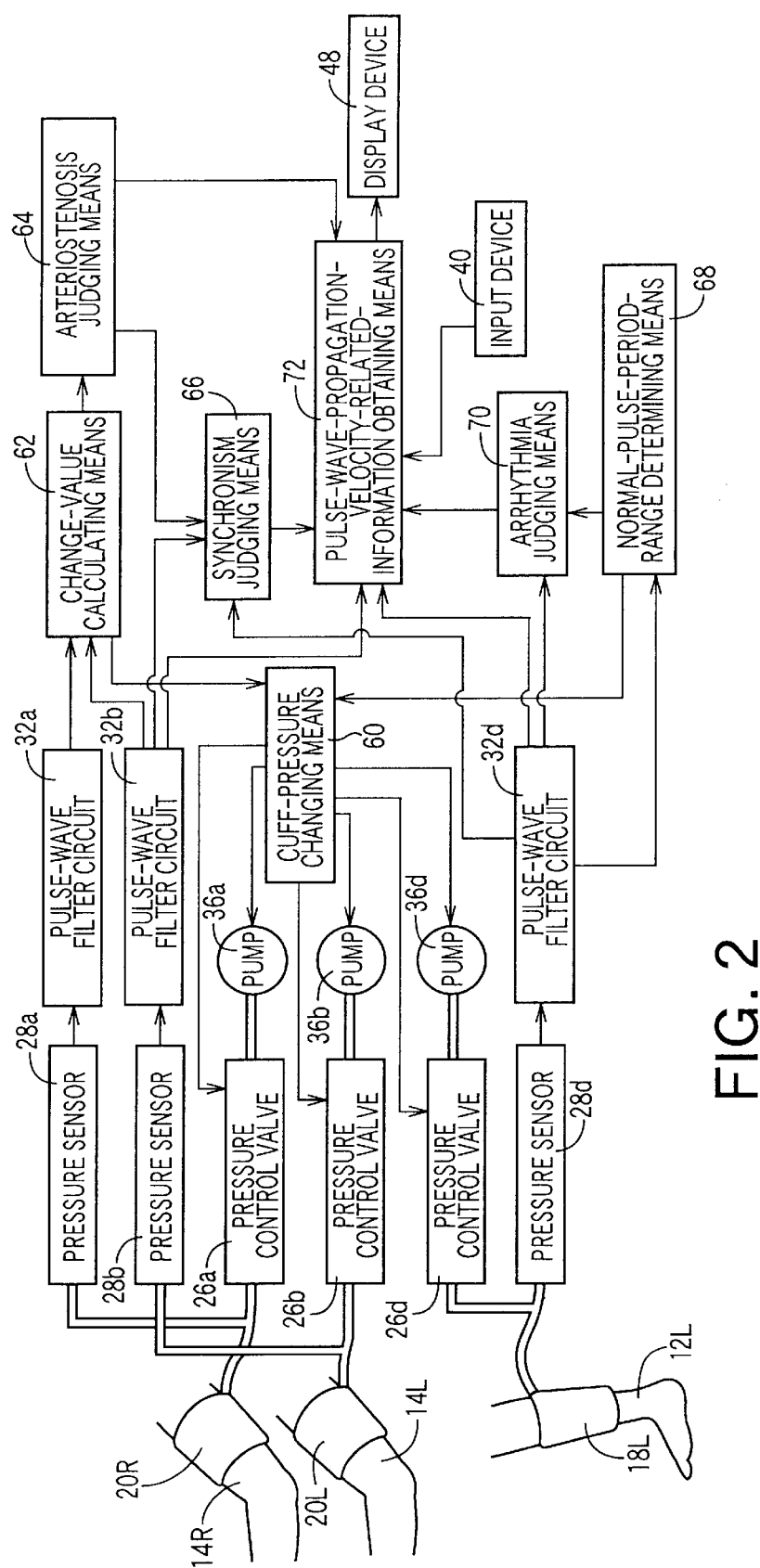
FIG. 2 is a diagrammatic view for explaining essential control functions of a CPU (central processing unit) of a control device, shown in FIG. 1, that relate to obtaining of pulse-wave-propagation-velocity-related information.

FIG. 2 is a diagrammatic view for explaining essential control functions of the CPU 42 that relate to obtaining of pulse-wave-propagation-related information. Since pulse-wave-propagation-related information is obtained in an identical manner with respect to each of the left ankle 12L and the right ankle 12R, the following description relates to the left ankle 12L as a representative of the two ankles.

A cuff-pressure changing means 60 controls, according to a command signal supplied from a change-value calculating means 62 or a pulse-wave-propagation-related-information obtaining means 72, each described later, the air pumps 36a, 36b, 36d and the pressure control valves 26a, 26b, 26d connected to those air pumps 36a, 36b, 36d, so as to control the left and right upper-arm cuff pressures $PC_b$, $PC_a$ and the left ankle cuff pressure $PC_d$.

The change-value calculating means 62 supplies, to the cuff-pressure changing means 60, respective command signals to command the changing means 60 to control each of the left and right upper-arm cuff pressures $PC_b$, $PC_a$ to a predetermined first target pressure, $PC_{M1}$, and a predetermined second target pressure $PC_{M2}$, so that in a state in which the two cuff pressures $PC_b$, $PC_a$ are held at the first target pressure $PC_{M1}$, the calculating means 62 reads in one or more heartbeat-synchronous pulses of each of the two upper-arm pulse waves $WB_L$, $WB_R$ supplied from the two pulse-wave filter circuits 32b, 32a and in a state in which the two cuff pressures $PC_b$, $PC_a$ are held at the second target pressure $PC_{M2}$, the calculating means 62 reads in one or more heartbeat-synchronous pulses of each of the two upper-arm pulse waves $WB_L$, $WB_R$ supplied from the two pulse-wave filter circuits 32b, 32a. Here, it is noted that the first target pressure $PC_{M1}$ is predetermined at a pressure equal to an average diastolic blood pressure, $BP_{BDIA}$, of an upper arm of a human being, and the second target pressure $PC_{M2}$ is predetermined at a pressure equal to an average mean blood pressure, $BP_{BMEAN}$, of the upper arm.

Then, the change-value calculating means 62 calculates a first change value based on the respective left upper-arm pulse waves $WB_L$ that have been read in when the left upper-arm cuff pressure $PC_b$ is held at the first and second target pressures $PC_{M1}$, $PC_{M2}$, and additionally calculates a second change value based on the respective right upper-arm pulse waves $WB_R$ that have been read in when the right upper-arm cuff pressure $PC_a$ is held at the first and second target pressures $PC_{M1}$, $PC_{M2}$. The first and second change values represent respective changes of respective shapes or forms of the left and right upper-arm pulse waves $WB_L$, $WB_R$ that are caused by the respective changes of the left and right upper-arm cuff pressures $PC_b$, $PC_a$. A change of a shape of a pulse wave may be a change of an amplitude, a degree of sharpness, or an increasing period, of a heartbeat-synchronous pulse of the pulse wave, and accordingly a change value may be an amount, or a rate, of change of respective amplitudes, respective degrees of sharpness, or respective increasing periods, of respective heartbeat-synchronous pulses of the pulse wave.

A degree of sharpness indicates a degree of upward projection of a heartbeat-synchronous pulse of a pulse wave. The sharpness degree may be a normalized pulse area VR (=S/(W×H)) which is obtained by dividing a pulse area S (=S1+S2) calculated by summarizing one heartbeat-synchronous pulse of upper-arm wave WB, shown in FIG. 3, over a pulse period W, by a product (W×H) of a height H of a peak point b and the pulse period W; a normalized value of a first-half area S1 calculated by summarizing a first half portion from a rising point a to the peak point b; a normalized value of a second-half area S2 calculated by summarizing a second half portion following the peak point b; or a normalized value I/W obtained by dividing, by the pulse period W, a width I of one heartbeat-synchronous pulse at a height equal to two thirds, H×(⅔), of the peak-point height H. Otherwise, the normalized pulse area VR may be replaced by a parameter % MAP (=100×G/H) that is obtained as a percentage of a height G of a center of gravity of the pulse area S relative to the peak-point height H, i.e., pulse pressure.

Figure 3:
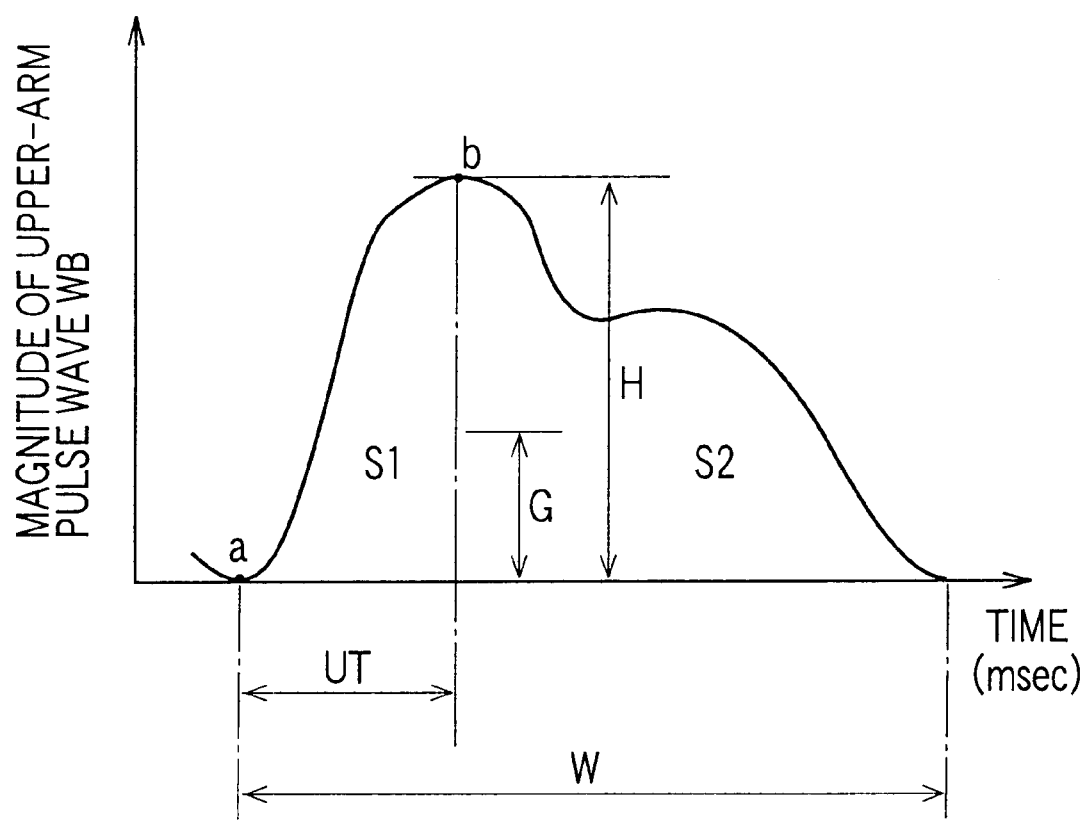
FIG. 3 is a graph showing an example of an upper-arm pulse wave WB.

As shown in FIG. 3, the magnitude of upper-arm pulse wave WB increases in the above-described increasing period, UT, of one heartbeat-synchronous pulse that starts with the rising point a and ends with the peak point b.

An arteriosclerosis judging means 64 has two functions. The first function of the arteriosclerosis judging means 64 is to judge whether the first change value determined by the change-value calculating means 62 is not smaller than a predetermined value, thereby judging whether the region between the heart and the left upper arm 14L has arteriosclerosis, and additionally judges whether the second change value also determined by the change-value calculating means 62 is not smaller than the predetermined value, thereby judging whether the region between the heart and the right upper arm 14R has arteriosclerosis. More specifically described, if the first or second change value is smaller than the predetermined value, the judging means 64 judges that the subject has arteriosclerosis; and if the change value is not smaller than the predetermined value, the judging means 64 judges that the subject does not have arteriosclerosis. The second function of the arteriosclerosis judging means 64 is to compare the first and second change values calculated by the change-value calculating means 62, with each other, thereby judging which is lower, a degree of arteriosclerosis of the region between the heart and the left upper arm 14L, or a degree of arteriosclerosis of the region between the heart and the right upper arm 14R. A blood pressure BP of a region located downstream of an arteriosclerotic region is lower than that of the arteriosclerotic region. In addition, as cuff pressure PC approaches a mean blood pressure, amplitude of pulse wave increases, i.e., shape of pulse wave becomes sharper. Therefore, the first and second change values, each of which has been calculated based on the respective shapes of the two pulse waves obtained at the two different cuff pressure values PC, reflect the respective degrees of arteriosclerosis of the respective regions located upstream of the left and right upper arms 14L, 14R. Thus, the arteriosclerosis judging means 64 can judge, by comparing the first and second change values with each other, which is lower, the degree of arteriosclerosis of the region between the heart and the left upper arm 14L, or the degree of arteriosclerosis of the region between the heart and the right upper arm 14R.

A synchronism judging means 66 judges whether the upper-arm pulse wave WB detected from the upper arm corresponding to the region whose degree of arteriosclerosis has been judged as being lower by the arteriosclerosis judging means 64 (e.g., the left-upper-arm pulse wave $WB_L$ in the example shown in FIG. 2) is synchronous with the left-ankle pulse wave $WA_L$. More specifically described, the synchronism judging means 66 determines respective characteristic points of the two pulse waves, e.g., respective rising points or respective peak points, and judges whether the respective characteristic points of the two pulse waves are synchronous with each other.

A normal-pulse-period-range determining means 68 reads in a plurality of heartbeat-synchronous pulses of any one of the left-upper-arm pulse wave $WB_L$, the right-upper-arm pulse wave $WB_R$, and the left-ankle pulse wave $WA_L$ (e.g., the left-ankle pulse wave $WA_L$ extracted by the pulse-wave filter circuit 32d in the example shown in FIG. 2), calculates an average value of respective pulse periods of those heartbeat-synchronous pulses, and determines, as a normal pulse-period range, a range whose middle value is equal to the average value and whose upper-limit and lower-limit values are equal to respective predetermined proportions (e.g., ±20%) of the average.

An arrhythmia judging means 70 reads in successive heartbeat-synchronous pulses of any one of the left-upper-arm pulse wave $WB_L$, the right-upper-arm pulse wave $WB_R$, and the left-ankle pulse wave $WA_L$ (e.g., the left-ankle pulse wave $WA_L$ in the example shown in FIG. 2), calculates respective pulse periods of those heartbeat-synchronous pulses, and judges whether each of the respective calculated pulse periods of those heartbeat-synchronous pulses falls within the normal pulse-period range determined by the normal-pulse-period-range determining means 68. If yes, the arrhythmia judging means 70 judges that the pulse wave is not arrhythmia; but, if not, the judging means 70 judges that the pulse wave is arrhythmia.

The pulse-wave-propagation-related-information obtaining means 72 supplies, to the cuff-pressure changing means 60, to respective command signals to control the upper-arm cuff pressure PC corresponding to the region whose degree of arteriosclerosis has been judged as being lower by the arteriosclerosis judging means 64, and the left-ankle cuff pressure $PC_d$, to respective predetermined pulse-wave detecting pressures; and, in a state in which the upper-arm cuff pressure PC and the left-ankle cuff pressure $PC_d$ are held at the respective pulse-wave detecting pressures, the obtaining means 72 continuously reads in the upper-arm pulse wave WB and the left-ankle pulse wave $WA_L$ detected from the respective cuffs 18, 20 whose pressures are held at the respective pulse-wave detecting pressures. The pulse-wave detecting pressures are predetermined at respective pressures which are lower than respective diastolic blood pressures of the respective regions where the cuffs 18, 20 are worn and which assure that the respective pulse-wave signals SM extracted by the respective pulse-wave filter circuits 32 have a sufficiently great magnitude, for example, are predetermined at 50 mmHg.

Then, the information obtaining means 72 obtains a piece of pulse-wave-propagation-related information based on the continuously read-in upper-arm pulse wave WB and left-ankle pulse wave $WA_L$ that have been judged as being synchronous with each other by the synchronism judging means 66 and have been judged as being not arrhythmia by the arrhythmia judging means 70. More specifically described, the information obtaining means 72 determines, as a pulse-wave propagation time DT (sec), a time difference between a time of occurrence of a prescribed point, such as a rising point or a peak point, of one heartbeat-synchronous pulse of the upper-arm pulse wave WB and a time of occurrence of a prescribed point of one heartbeat-synchronous pulse of the left-ankle pulse wave $WA_L$ that corresponds to the prescribed point of the upper-arm pulse wave WB.

Moreover, the information obtaining means 72 determines a propagation distance L, based on the patient's height T input through the input device 40, according to a relationship between height T and propagation distance L, represented by the following Expression 1 pre-stored in the ROM 44, and finally determines a pulse-wave propagation velocity PWV (cm/sec), based on the thus determined propagation distance L and pulse-wave propagation time DT, according to the following Expression 2 pre-stored in the ROM 44:

$$L=\alpha T+\beta \quad \text{(Expression 1)}$$

where $\alpha$ and $\beta$ are constants that are experimentally obtained.

$$PWV=L/DT \quad \text{(Expression 2)}$$

The propagation distance L is substantially equal to a difference between a distance between the patient's heart and the upper arm 14 where the upper-arm cuff 20 is worn, and a distance between the patient's heart and the left ankle 12L where the left-ankle cuff 18L is worn. The information obtaining means 72 operates the display device 48 to display the thus determined pulse-wave propagation time DT or pulse-wave propagation velocity PWV.

Figure 4:
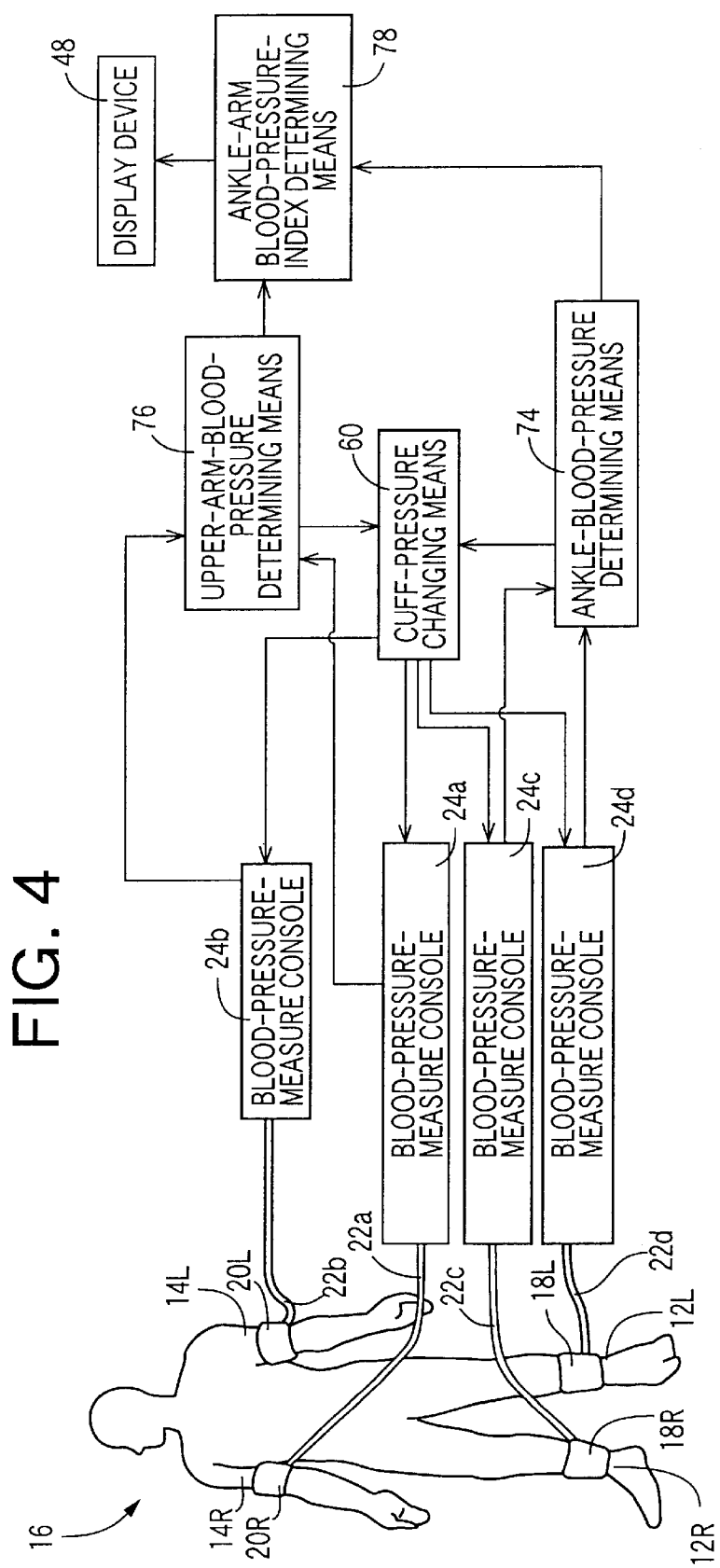
FIG. 4 is a diagrammatic view for explaining essential control functions of the CPU of FIG. 1 that relate to calculation of ABI (ankle arm blood pressure index)

FIG. 4 is a diagrammatic view for explaining the essential control functions of the CPU 42 that relate to the calculation of ABI. An ankle-blood-pressure determining means 74 supplies, to the cuff-pressure changing means 60, a command signal to increase quickly the left-ankle cuff pressure $PC_d$ and the right-ankle cuff pressure $PC_c$ up to a predetermined first target deflation-start pressure (e.g., 240 mmHg) and subsequently decrease slowly those pressures $PC_d$, $PC_c$ at a rate of, e.g., from 3 to 5 mmHg/sec. Based on change of respective amplitudes of respective heartbeat-synchronous pulses of the left-ankle pulse wave $WA_L$ continuously obtained during the slow deflation of the left-ankle cuff 18L and change of respective amplitudes of respective heartbeat-synchronous pulses of the right-ankle pulse wave $WA_R$ continuously obtained during the slow deflation of the right-ankle cuff 18R, the determining means 74 determines, according to well-known oscillometric method, blood-pressure values BP of the left ankle 12L, i.e., a left-ankle systolic blood pressure $BP_{ASYS}(L)$, a left-ankle mean blood pressure $BP_{AMEAN}(L)$, and a left-ankle diastolic blood pressure $BP_{ADIA}(L)$, and blood-pressure values BP of the right ankle 12R, i.e., a right-ankle systolic blood pressure $BP_{ASYS}(R)$, a right-ankle mean blood pressure $BP_{AMEAN}(R)$, and a right-ankle diastolic blood pressure $BP_{ADIA}(R)$.

An upper-arm-blood-pressure determining means 76 supplies, to the cuff-pressure changing means 60, a command signal to increase quickly the left-upper-arm cuff pressure $PC_b$ and the right-upper-arm cuff pressure $PC_a$ up to a predetermined second target deflation-start pressure (e.g., 180 mmHg) and subsequently decrease slowly those pressures $PC_b$, $PC_a$ at a rate of from 3 to 5 mmHg/sec. Based on change of respective amplitudes of respective heartbeat-synchronous pulses of the left-upper-arm pulse wave $WB_L$ continuously obtained during the slow deflation of the left-upper-arm cuff 20L and change of respective amplitudes of respective heartbeat-synchronous pulses of the right-upper-arm pulse wave $WB_R$ continuously obtained during the slow deflation of the right-upper-arm cuff 20R, the determining means 76 determines, according to well-known oscillometric method, blood-pressure values BP of the left upper-arm 14L, i.e., a left-upper-arm systolic blood pressure $BP_{BSYS}(L)$, a left-upper-arm mean blood pressure $BP_{BMEAN}(L)$, and a left-upper-arm diastolic blood pressure $BP_{BDIA}(L)$, and blood-pressure values BP of the right upper-arm 14R, i.e., a right upper-arm systolic blood pressure $BP_{BSYS}(R)$, a right-upper-arm mean blood pressure $BP_{BMEAN}(R)$, and a right-upper-arm diastolic blood pressure $BP_{BDIA}(R)$.

An ankle-arm blood-pressure-index calculating means 78 divides the left-ankle systolic blood pressure $BP_{ASYS}(L)$ determined by the ankle-blood-pressure determining means 74, by the left-upper-arm systolic blood pressure $BP_{BSYS}(L)$ determined by the upper-arm-blood-pressure determining means 76, and thereby calculates a left ankle-arm blood-pressure index ABI (L), and additionally divides the right-ankle systolic blood pressure $BP_{ASYS}(R)$ determined by the ankle-blood-pressure determining means 74, by the right-upper-arm systolic blood pressure $BP_{BSYS}(R)$ determined by the upper-arm-blood-pressure determining means 76, and thereby calculates a right ankle-arm blood-pressure index ABI(R). In addition, the index calculating means 84 operates the display device 48 to display the thus calculated left and right ankle-arm blood-pressure indexes ABI(L), ABI(R), together with the pulse-wave-propagation-velocity-related information obtained by the pulse-wave-propagation-velocity-related-information obtaining means 72.

Figure 5:
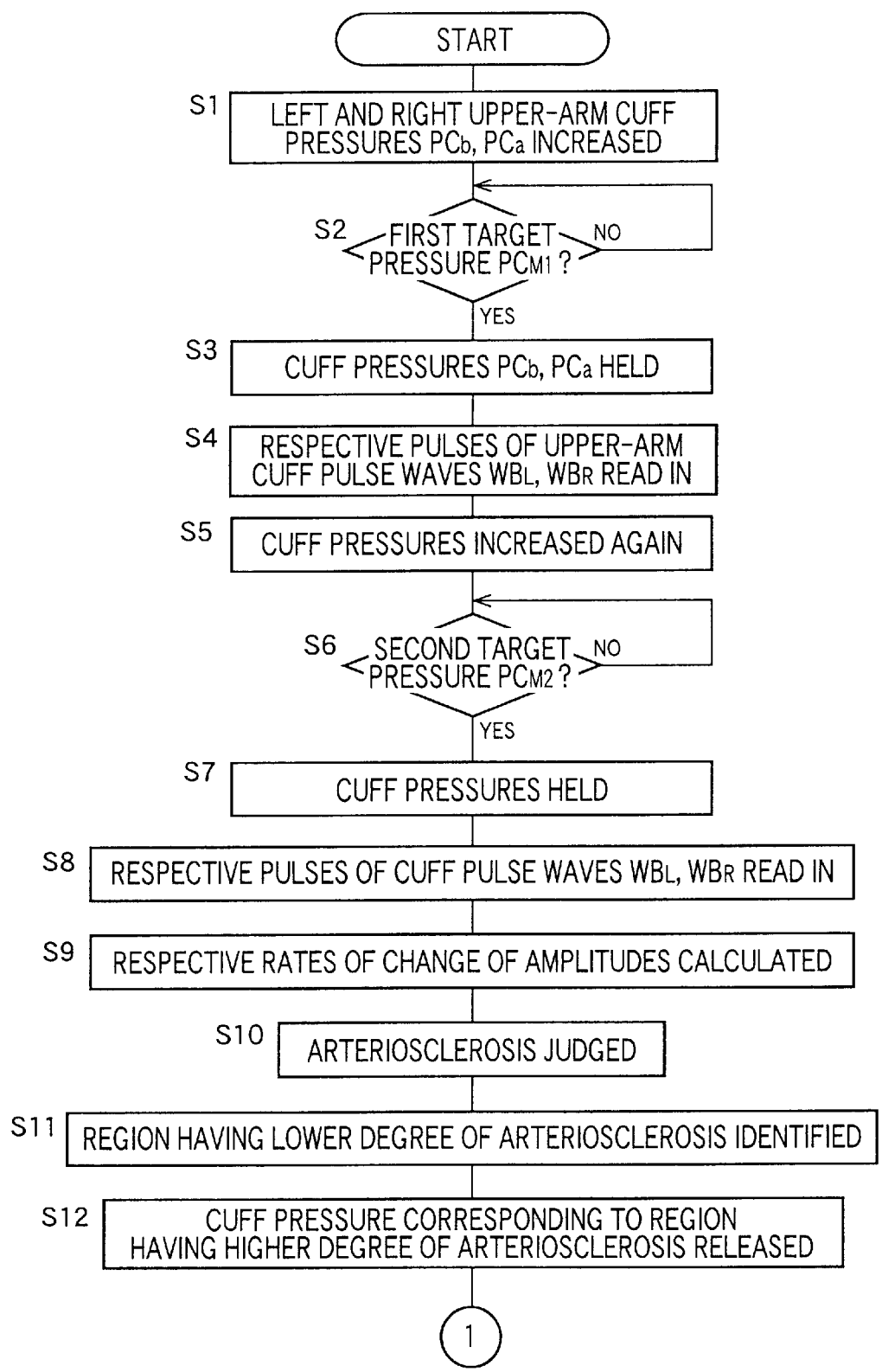
FIG. 5 is a flow chart representing the essential control functions of the CPU, shown in FIG. 2, that relate to the obtaining of pulse-wave-propagation-velocity-related information.
Figure 6:
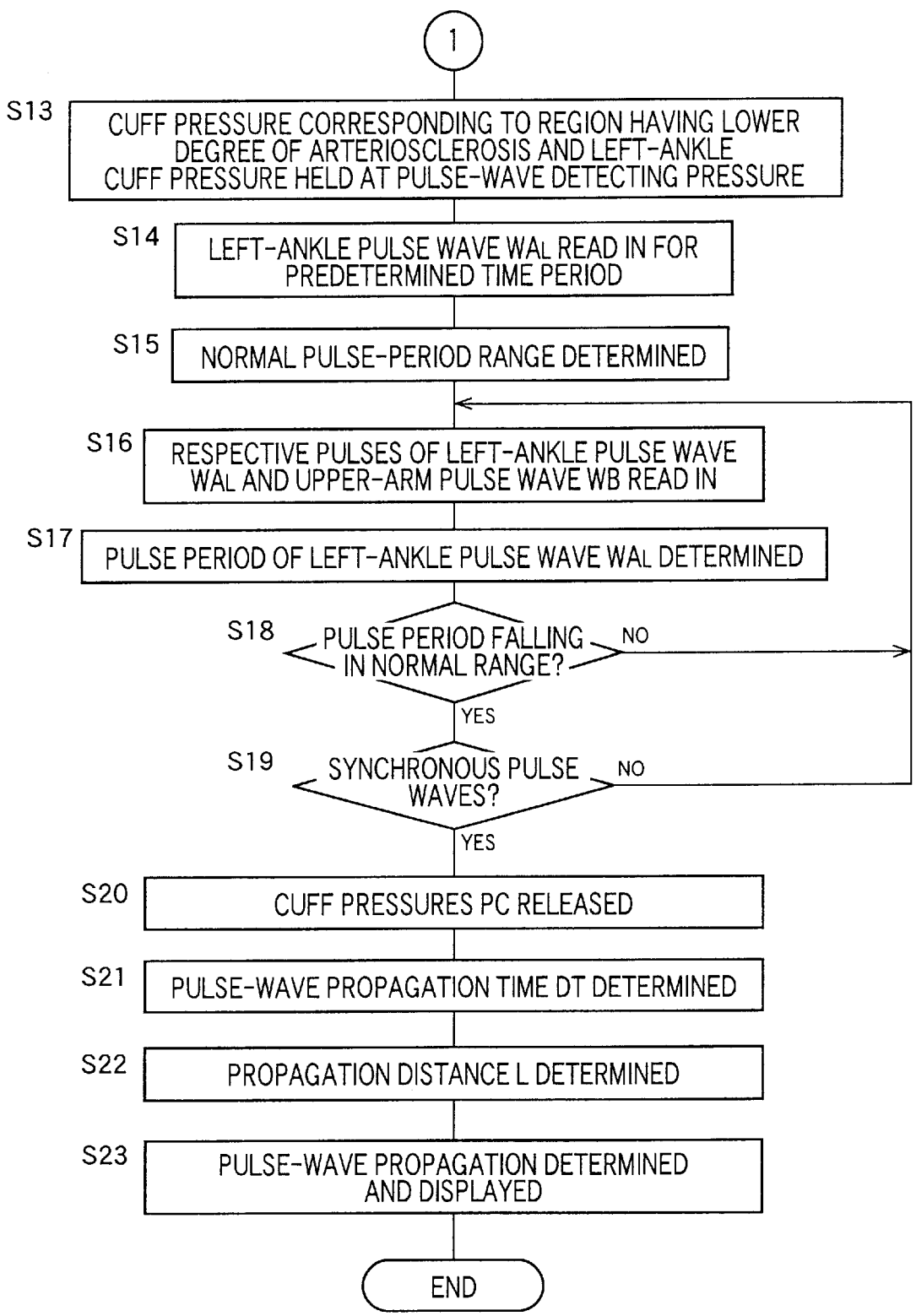
FIG. 6 is a flow chart representing a routine following the routine represented by the flow chart of FIG. 5.

FIGS. 5 and 6 are flow charts representing the essential control functions of the CPU 42, shown in FIGS. 2 and 4, that relate to the obtaining of pulse-wave-propagation-velocity-related information. The flow charts of FIGS. 5 and 6 are started upon operation of a start button, not shown, on an assumption that the height signal ST representing the patient's height T has been supplied from the input device 40 to the CPU 42.

First, at Step S1 of FIG. 5 (hereinafter, "Step(s)" are omitted), the CPU 42 controls the air pumps 36a, 36b and the pressure control valves 26a, 26b to start increasing quickly the left and right upper-arm cuff-pressures $PC_b$, $PC_a$. Then, at S2, the CPU judges whether the upper-arm cuff-pressures $PC_b$, $PC_a$ have been increased up to the first target pressure $PC_{M1}$ predetermined at 60 mmHg. If a negative judgment is made at S2, the CPU repeats S2 while continuing increasing the upper-arm cuff-pressures $PC_b$, $PC_a$. Meanwhile, if a positive judgment is made at S2, the control goes to S3 to control the pressure control valves 26a, 26b to maintain the upper-arm cuff-pressures $PC_b$, $PC_a$ at the first target pressure $PC_{M1}$.

Then, at S4, in a state in which the upper-arm cuff-pressures $PC_b$, $PC_a$ are held at the second target pressure $PC_{M2}$, the CPU reads in one heartbeat-synchronous pulse of the left-upper-arm pulse wave $WB_L$ supplied from the pulse-wave filter circuit 32b and one heartbeat-synchronous pulse of the right-upper-arm pulse wave $WB_R$ supplied from the pulse-wave filter circuit 32a. After that, the control goes to S5 to control the pressure control valves 26a, 26b to start increasing quickly the left and right upper-arm cuff-pressures $PC_b$, $PC_a$.

Then, at S6, the CPU judges whether the upper-arm cuff-pressures $PC_b$, $PC_a$ have been increased up to the second target pressure $PC_{M2}$ predetermined at 90 mmHg. If a negative judgment is made at S6, the CPU repeats S6 while continuing increasing the upper-arm cuff-pressures $PC_b$, $PC_a$. Meanwhile, if a positive judgment is made at S6, the control goes to S7 to control the pressure control valves 26a, 26b to maintain the upper-arm cuff-pressures $PC_b$, $PC_a$ at the second target pressure $PC_{M2}$.

Then, at S8, in a state in which the upper-arm cuff-pressures $PC_b$, $PC_a$ are held at the second target pressure $PC_{M2}$, the CPU reads in one heartbeat-synchronous pulse of the left-upper-arm pulse wave $WB_L$ and one heartbeat-synchronous pulse of the right-upper-arm pulse wave $WB_R$. After that, the control goes to S9 to calculate, as a first change value, a rate of change of respective amplitudes of the respective heartbeat-synchronous pulses of the left-upper-arm pulse wave $WB_L$ that have been detected with the left-upper-arm cuff pressure $PC_b$ being held at 60 mmHg and 90 mmHg, and calculate, as a second change value, a rate of change of respective amplitudes of the respective heartbeat-synchronous pulses of the right-upper-arm pulse wave $WB_R$ that have been detected with the right-upper-arm cuff pressure $PC_a$ being held at 60 mmHg and 90 mmHg. More specifically described, first, the CPU determines respective amplitudes of the respective heartbeat-synchronous pulses of the left and right upper-arm pulse waves $WB_L$, $WB_R$ that have been read in at S4, and determines respective amplitudes of the respective heartbeat-synchronous pulses of the left and right upper-arm pulse waves $WB_L$, $WB_R$ that have been read in at S8. Then, the CPU divides the amplitude of the pulse of the left-upper-arm pulse wave $WB_L$, read in at S8 where the left-upper-arm cuff pressure $PC_b$ is held at the second target pressure $PC_{M2}$, by the amplitude of the pulse of the left-upper-arm pulse wave $WB_L$, read in at S4 where the left-upper-arm cuff pressure $PC_b$ is held at the first target pressure $PC_{M1}$, thereby calculating, as the first change value, the rate of change of the amplitudes of the respective pulses of the left upper-arm pulse wave $WB_L$. Similarly, the CPU divides the amplitude of the pulse of the right-upper-arm pulse wave $WB_R$, read in at S8 where the right-upper-arm cuff pressure $PC_a$ is held at the second target pressure $PC_{M2}$, by the amplitude of the pulse of the right-upper-arm pulse wave $WB_R$, read in at S4 where the right-upper-arm cuff pressure $PC_a$ is held at the first target pressure $PC_{M1}$, thereby calculating, as the second change value, the rate of change of the amplitudes of the respective pulses of the right upper-arm pulse wave $WB_R$. In FIG. 5, S4, S8, and S9 corresponds to the change-value calculating means 62.

Subsequently, the control goes to S10 and S11 corresponding to the arteriosclerosis judging means 64. At S10, the CPU judges whether the rate of change of amplitudes as the first change value is not smaller than a predetermined value, thereby judging whether the region between the heart and the left upper arm 14L has arteriosclerosis, and additionally judges whether the rate of change of amplitudes as the second change value is not smaller than the predetermined value, thereby judging whether the region between the heart and the right upper arm 14R has arteriosclerosis. More specifically described, if the rate of change as the first or second change value calculated at S9 is smaller than the predetermined value, the CPU judges that the subject has arteriosclerosis; and if the rate of change is not smaller than the predetermined value, the CPU judges that the subject does not have arteriosclerosis. The reason why arteriosclerosis can be judged in the above-described manner is as follows: The first and second target pressures $PC_{M1}$, $PC_{M2}$ are predetermined at respective values around respective average upper-arm diastolic and mean blood-pressure values $BP_{BDIA}$, $BP_{BMEAN}$, and the respective amplitudes of the two upper-arm pulse waves WB detected as the respective oscillatory components of the respective pressures of the two cuffs 20, continuously increase till the two cuff pressures PC increase up to the mean blood-pressure value $BP_{BMEAN}$. Therefore, if the subject does not have arteriosclerosis, the rate of change of amplitudes as the first or second change value should be a considerably great value. On the other hand, if the subject has arteriosclerosis in the region between the heart and the left or right upper arm 14, the upper-arm blood pressure $BP_B$ measured from the upper arm 14 should be so low that the second target pressure $PC_{M2}$ is higher than the mean blood pressure $BP_{BMEAN}$ and accordingly the amplitude of the upper-arm pulse wave WB should be small. Thus, if the subject has arteriosclerosis in the region between the heart and the upper arm 14, then the rate of change of amplitudes as the first or second change value should be a considerably small value. In this way, arteriosclerosis can be judged based on the rate of change of amplitudes.

Subsequently, at S11, the CPU compares the rate of change of amplitudes of the left upper-arm pulse wave $WB_L$ and the rate of change of amplitudes of the right upper-arm pulse wave $WB_R$, both calculated at S9, with each other, thereby judging which one of the two rates of change is greater. Thus, the CPU judges that a degree of arteriosclerosis of one of the region between the heart and one upper arm 14 and the region between the heart and the other upper arm 14, which one region corresponds to the greater rate of change, is lower than that of the other region. Then, at S12, the CPU releases the cuff pressure PC of the cuff 20 worn on the upper arm 14 corresponding to the other region opposite to the one region identified at S11.

Next, the control proceeds with S13 and the following steps shown in FIG. 6. At S13, the CPU operates for controlling the upper-arm cuff pressure PC corresponding to the region whose degree of arteriosclerosis has been judged as being lower at S11, and the left ankle cuff pressure $PC_d$, each to the pulse-wave detecting pressure predetermined at 50 mmHg.

Then, the control goes to S14 and S15 corresponding to the normal-pulse-period-range determining means 68. At S14, the CPU reads in a plurality of heartbeat-synchronous pulses of the left-ankle pulse wave $WA_L$, for a predetermined time period corresponding to, e.g., several to ten and several heartbeats. Then, at S15, the CPU determines respective periods of the respective heartbeat-synchronous pulses of the left-ankle pulse wave $WA_L$ read in at S14, and determines a normal pulse-period range whose middle value is equal to an average of the thus determined pulse periods and whose upper and lower limit values are equal to ±20% of the average pulse period, respectively.

Then, at S16, the CPU reads in one heartbeat-synchronous pulse of the left-ankle pulse wave $WA_L$ represented by the pulse-wave signal SM supplied from the pulse-wave filter circuit 32 connected to the cuff 18 whose pressure PC is held at the pulse-wave detecting pressure at S13, and one heartbeat-synchronous pulse of the left or right upper-arm pulse wave $WB_L$, $WB_R$ (hereinafter, referred to as the upper-arm pulse wave WB) represented by the pulse-wave signal SM supplied from the pulse-wave filter circuit 32 connected to the cuff 20 whose pressure PC is also held at the pulse-wave detecting pressure at S13. Subsequently, the control goes to S17 and S18 corresponding to the arrhythmia judging means 70. At S17, the CPU determines a period of the one heartbeat-synchronous pulse of the left-ankle pulse wave $WA_L$ read in at S16 and, at S18, the CPU judges whether the pulse period determined at S17 falls within the normal pulse-period range determined at S15. If a negative judgment is made at S18, the CPU judges that the one pulse read in at S16 is an arrhythmic pulse that cannot be used to determine an accurate pulse-wave propagation time DT. Hence, the control goes back to S16 to read in new pulse waves.

On the other hand, if a positive judgment is made at S18, the control goes to S19 corresponding to the synchronism judging means 66. More specifically described, the CPU determines respective rising points and peak points of the respective heartbeat-synchronous pulses of the left-ankle pulse wave $WA_L$ and the upper-arm pulse wave WB, read in at S16, and determines a time difference between the thus determined two rising points and a time difference between the thus determined two peak points. If the thus determined two time differences are substantially equal to each other, the CPU judges that the left-ankle pulse wave $WA_L$ and the upper-arm pulse wave WB are synchronous with each other, and the control goes to S20. On the other hand, if not, noise produced by a physical motion of the subject may have been mixed with one of the two pulse waves and consequently an erroneous point has been identified as one of the two rising points or one of the two peak points. Hence, the control goes back to S16 to read in noise-free pulse waves.

If a positive judgment is made at S19, the control goes to S20 to stop the air pumps 36 and operate the pressure control valves 26 to release the cuff pressures PC down to an atmospheric pressure.

Then, the control goes to S21 to S23 corresponding to the pulse-wave-propagation-velocity-relating-information obtaining means 72. First, at S21, the CPU determines the rising point of the one pulse of the left-ankle pulse wave $WA_L$ read at S16, and determines the rising point of the one pulse of the upper-arm pulse wave WB also read at S16. In addition, the CPU determines, as a pulse-wave propagation time DT, a time difference between the respective times of occurrence of the respective rising points of the two pulse waves $WA_L$, WB. Then, the control goes to S22 to substitute the patient's height T supplied in advance, for the corresponding variable of the above-indicated Equation 1, and thereby determine a propagation distance L. Subsequently, the control goes to S23 to substitute the pulse wave propagation time DT determined at S21 and the propagation distance L determined at S22, for the corresponding variables of the above-indicated Equation 2, and thereby determine a pulse-wave propagation velocity PWV. The CPU operates the display device 48 to display the thus determined velocity PWV.

The ankle-arm blood-pressure-index calculating means 78, shown in FIG. 4, calculates an ABI value before or after the flow charts of FIGS. 5 and 6 are executed.

In the embodiment employing the flow charts shown in FIGS. 5 and 6, the CPU can judge, at S10 (the arteriosclerosis judging means 64), whether the upstream region located upstream of the region around which the upper-arm cuff 20L, 20R is wound has arteriosclerosis, based on the change of amplitudes of the upper-arm pulse wave $WB_L$, $WB_R$ with respect to the change of pressing pressure of the cuff 20L, 20R, because, if the upstream region has arteriosclerosis, the amplitudes of the pulse wave $WB_L$, $WB_R$, extracted by the pulse-wave filter circuit 32b, 32a, significantly decrease at a lower pressing pressure of the cuff 20L, 20R than a pressing pressure at which the amplitudes of the pulse wave $WB_L$, $WB_R$ detected from the upstream region which is free of arteriosclerosis significantly decrease.

In addition, in the embodiment employing the flow charts shown in FIGS. 5 and 6, the CPU calculates, at S9 (the change-value calculating means 62), the first and second change values. Since the first change value represents the change of amplitudes of the left-upper-arm pulse wave $WB_L$ with respect to the change of the left-upper-arm cuff pressure $PC_b$, and the second change value represents the change of amplitudes of the right-upper-arm pulse wave $WB_R$ with respect to the change of the right-upper-arm cuff pressure $PC_a$, the first change value reflects a degree of arteriosclerosis of the region between the heart and the left upper arm 14L and the second change value reflects a degree of arteriosclerosis of the region between the heart and the right upper arm 14R. Thus, the CPU can judge, at S11 (the arteriosclerosis judging means 64), which is lower, the degree of arteriosclerosis of the region between the heart and the left upper arm 14L or the degree of arteriosclerosis of the region between the heart and the right upper arm 14R, by comparing the first and second change values with each other. Then, the CPU determines, at S21 to S23 (the pulse-wave-propagation-velocity-related-information obtaining means 72), the pulse-wave propagation velocity PWV based on the upper-arm pulse wave WB corresponding to the region judged as having the lower degree of arteriosclerosis, and the left-ankle pulse wave $WA_L$. Thus, the present apparatus can obtain the pulse-wave propagation velocity PWV that is less influenced by the arteriosclerosis of the upper arm 14. Therefore, arteriosclerosis of an inferior limb of a living subject can be accurately diagnosed based on the accurate pulse-wave propagation velocity PWV.

When noise is produced by a physical motion of a living subject, it may be mixed, at different timings, with two pulse waves detected from different regions of the subject. In this case, respective detected pulses of the two pulse waves may not be synchronous with each other. This problem is avoided in the embodiment employing the flow charts shown in FIGS. 5 and 6, wherein the CPU judges, at S19 (the synchronism judging means 66), whether the upper-arm pulse wave WB extracted by the pulse-wave filter circuit 32a, 32b and the left-ankle pulse wave $WA_L$ extracted by the pulse-wave filter circuit 32d are synchronous with each other. If a positive judgment is made, it can be said that the upper-arm pulse wave WB and the left-ankle pulse wave $WA_L$ are free of the noise produced by the physical motion of the subject. Therefore, the CPU determines, at S21 to S23 (the pulse-wave-propagation-velocity-related-information obtaining means 72), the pulse-wave propagation velocity PWV based on the upper-arm pulse wave WB and the left-ankle pulse wave $WA_L$ that have been judged as being synchronous with each other at S19 (the synchronism judging means 66). Thus, the present apparatus can obtain the accurate pulse-wave propagation velocity PWV. Therefore, arteriosclerosis can be accurately diagnosed based on the thus obtained, accurate pulse-wave propagation velocity PWV.

Moreover, in the embodiment employing the flow charts shown in FIGS. 5 and 6, the CPU determines, at S21 to S23 (the pulse-wave-propagation-velocity-related-information obtaining means 72), the pulse-wave propagation velocity PWV based on the upper-arm pulse wave WB and the left-ankle pulse wave $WA_L$ that have been judged as being not arrhythmic at S17 and S18 (the arrhythmia judging means 70). Thus, the present apparatus can obtain the accurate pulse-wave propagation velocity PWV. Therefore, arteriosclerosis can be accurately diagnosed based on the thus obtained, accurate pulse-wave propagation velocity PWV.

While the present invention has been described in detail in its preferred embodiments by reference to the drawings, it is to be understood that the present invention is by no means limited to the details of those embodiments and may be embodied with other changes, improvements and modifications that may occur to a person skilled in the art without departing from the spirit and scope of the invention defined in the appended claims.

What is claimed is:

1. An apparatus for diagnosing arteriosclerosis of a living subject, comprising:

an inflatable cuff which is adapted to be wound around a first portion of the subject to press said first portion with a pressing pressure;

a pulse-wave detecting device which detects a pulse wave that is produced from an artery of said first portion of the subject pressed by the cuff with the pressing pressure and is transmitted to the cuff; and an arteriosclerosis judging means for judging, based on a change of the pulse wave caused by a change of the pressing pressure of the cuff, whether there is an arteriosclerotic lesion in a second portion of the subject that is located upstream of said first portion in a direction in which blood flows in the artery.

2. An apparatus according to claim 1, wherein the arteriosclerosis judging means comprises:

means for holding the pressing pressure of the cuff at a first target pressure around a diastolic blood pressure of said first portion of the subject;

means for reading in a first heartbeat-synchronous pulse of the pulse wave detected by the pulse-wave detecting device from the artery of said first portion pressed by the cuff whose pressing pressure is held at the first target pressure;

means for holding the pressing pressure of the cuff at a second target pressure around a mean blood pressure of said first portion of the subject;

means for reading in a second heartbeat-synchronous pulse of the pulse wave detected by the pulse-wave detecting device from the artery of said first portion pressed by the cuff whose pressing pressure is held at the second target pressure; and means for determining, as said change of the pulse wave, a change of a shape of the second heartbeat-synchronous pulse from a shape of the first heartbeat-synchronous pulse with respect to a change of the second target pressure from the first target pressure.

3. An apparatus according to claim 2, wherein the arteriosclerosis judging means further comprises means for judging whether a change value representing the change of the shape of the second heartbeat-synchronous pulse from the shape of the first heartbeat-synchronous pulse is smaller than a reference value and judging, when a positive judgment is made, that there is an arteriosclerotic lesion in said second portion of the subject.

4. An apparatus for diagnosing arteriosclerosis of an inferior limb of a living subject, comprising:

a left-superior-limb cuff which is adapted to be wound around a left superior limb of the subject to press the left superior limb with a first pressing pressure;

a right-superior-limb cuff which is adapted to be wound around a right superior limb of the subject to press the right superior limb with a second pressing pressure;

an inferior-limb cuff which is adapted to be wound around the inferior limb of the subject;

a left-superior-limb pulse-wave detecting device which detects, as a left-superior-limb pulse wave, a pulse wave which is produced from an artery of the left superior limb pressed by the left-superior-limb cuff with the first pressing pressure and is transmitted to the left-superior-limb cuff;

a right-superior-limb pulse-wave detecting device which detects, as a right-superior-limb pulse wave, the pulse wave which is produced from an artery of the right superior limb pressed by the right-superior-limb cuff with the second pressing pressure and is transmitted to the right-superior-limb cuff;

an inferior-limb pulse-wave detecting device which detects, as an inferior-limb pulse wave, the pulse wave which is produced from an artery of the inferior limb pressed by the inferior-limb cuff and is transmitted to the inferior-limb cuff;

a change-value calculating means for calculating a first change value representing a change of the left-superior-limb pulse wave caused by a change of the first pressing pressure of the left-superior-limb cuff, and a second change value representing a change of the right-superior-limb pulse wave caused by a change of the second pressing pressure of the right-superior-limb cuff;

an arteriosclerosis judging means for judging, based on a comparison of the first and second change values calculated by the change-value calculating means, which is lower, a degree of arteriosclerosis of a first portion of the subject located between the heart of the subject and the left superior limb or a degree of arteriosclerosis of a second portion of the subject located between the heart and the right superior limb; and a pulse-wave-propagation-velocity-related-information obtaining means for obtaining, based on (a) one of the left-superior-limb pulse wave and the right-superior-limb pulse wave that corresponds to one of the first and second portions that has the degree of arteriosclerosis judged as being lower than the degree of arteriosclerosis of the other of the first and second portions by the arteriosclerosis judging means, and (b) the inferior-limb pulse wave detected by the inferior-limb pulse-wave detecting device, pulse-wave-propagation-velocity-related information that is related to a velocity at which the pulse wave propagates in the subject.

5. An apparatus according to claim 4, wherein the change-value calculating means comprises:

means for holding the first and second pressing pressures of the left and right superior-limb cuffs at a first target pressure around respective diastolic blood pressures of the left and right superior limbs of the subject;

means for reading in respective first heartbeat-synchronous pulses of the left and right superior-limb pulse waves detected by the left and right superior-limb pulse-wave detecting devices from the respective arteries of the left and right superior limbs pressed by the left and right superior-limb cuffs whose first and second pressing pressures are held at the first target pressure;

means for holding the first and second pressing pressures of the left and right superior-limb cuffs at a second target pressure around respective mean blood pressures of the left and right superior limbs of the subject;

means for reading in respective second heartbeat-synchronous pulses of the left and right superior-limb pulse waves detected by the left and right superior-limb pulse-wave detecting devices from the respective arteries of the left and right superior limbs pressed by the left and right superior-limb cuffs whose first and second pressing pressures are held at the second target pressure; and means for determining, as the respective changes of the left and right superior-limb pulse waves, respective changes of respective shapes of the respective second heartbeat-synchronous pulses from respective shapes of the respective first heartbeat-synchronous pulses, each with respect to a change of the second target pressure from the first target pressure.

6. An apparatus for diagnosing arteriosclerosis of a living subject, comprising:

a first-pulse-wave detecting device including a first detecting portion which is adapted to be worn on a first body portion of the subject to detect, as a first pulse wave, a pulse wave produced from the first body portion;

a second-pulse-wave detecting device including a second detecting portion which is adapted to be worn on a second body portion of the subject to detect, as a second pulse wave, the pulse wave produced from the second body portion;

a synchronism judging means for judging whether the first pulse wave detected by the first-pulse-wave detecting device and the second pulse wave detected by the second-pulse-wave detecting device are synchronous with each other; and a pulse-wave-propagation-velocity-related-information obtaining means for obtaining, based on the first and second pulse waves judged as being synchronous with each other by the synchronism judging means, pulse-wave-propagation-velocity-related information that is related to a velocity at which the pulse wave propagates in the subject.

7. An apparatus for diagnosing arteriosclerosis of a living subject, comprising:

a first-pulse-wave detecting device including a first detecting portion which is adapted to be worn on a first body portion of the subject to detect, as a first pulse wave, a pulse wave produced from the first body portion;

a second-pulse-wave detecting device including a second detecting portion which is adapted to be worn on a second body portion of the subject to detect, as a second pulse wave, the pulse wave produced from the second body portion;

a normal-pulse-period-range determining means for determining a normal pulse-period range based on one of the first pulse wave detected by the first-pulse-wave detecting device and the second pulse wave detected by the second-pulse-wave detecting device;

an arrhythmia judging means for judging, when one of a pulse period of the first pulse wave and a pulse period of the second pulse wave falls in the normal pulse-period range determined by the normal-pulse-period-range determining means, that the first and second pulse waves are not arrhythmic; and a pulse-wave-propagation-velocity-related-information obtaining means for obtaining, based on the first and second pulse waves judged as being not arrhythmic by the arrhythmia judging means, pulse-wave-propagation-velocity-related information that is related to a velocity at which the pulse wave propagates in the subject.

8. An apparatus according to claim 5, wherein the arteriosclerosis judging means comprises means for judging which one of the first and second change values is greater than the other of the first and second change values, and judging that one of the first and second portions of the subject that corresponds to one of the first and second change values that is greater than the other of the first and second change values has a lower degree of arteriosclerosis than a degree of arteriosclerosis of the other of the first and second portions.

9. An apparatus according to claim 6, wherein the synchronism judging means comprises:

means for determining respective first characteristic points of respective heartbeat-synchronous pulses of the first pulse wave detected by the first-pulse-wave detecting device and the second pulse wave detected by the second-pulse-wave detecting device, and respective second characteristic points of the respective heartbeat-synchronous pulses of the first and second pulse waves;

means for determining a first time difference between respective times of occurrence of the respective first characteristic points, and a second time difference between respective times of occurrence of the respective second characteristic points; and means for judging whether the first and second time differences are substantially equal to each other and, when a positive judgment is made, judging that the first and second pulse waves are synchronous with each other.

10. An apparatus according to claim 7, wherein the normal-pulse-period-range determining means comprises:

means for determining respective pulse periods of a plurality of heartbeat-synchronous pulses of said one of the first pulse wave detected by the first-pulse-wave detecting device and the second pulse wave detected by the second-pulse-wave detecting device;

means for determining an average of the determined pulse periods; and means for determining the normal pulse-period range whose middle value is equal to the determined average and whose upper and lower limit values are determined based on the determined average.

* * * * *